US012639484B2

(12) United States Patent (10) Patent No.: US 12,639,484 B2

Shahar et al. (45) Date of Patent: May 26, 2026

(54) EAR-WEARABLE DEVICE MODELING

(71) Applicant: Starkey Laboratories, Inc., Eden Prairie, MN (US)

(72) Inventors: Amit Shahar, Hod Hasharon (IL); Lior Weizman, Tel Aviv (IL); Deepak Kadetotad, Tempe, AZ (US); Jinjun Xiao, Chanhassen, MN (US); Nitzan Bornstein, Tel Aviv (IL)

(73) Assignee: Starkey Laboratories, Inc., Eden Prairie, MN (US)

( * ) Notice: Subject to any disclaimer, the term of this patent is extended or adjusted under 35 U.S.C. 154(b) by 214 days.

(21) Appl. No.: 18/304,996

(22) Filed: Apr. 21, 2023

(65) Prior Publication Data

US 2023/0351064 A1      Nov. 2, 2023

Related U.S. Application Data

(60) Provisional application No. 63/363,870, filed on Apr. 29, 2022.

(51) Int. Cl.
A61F 11/00      (2022.01)
A61F 11/06      (2006.01)
G06F 30/00      (2020.01)

(52) U.S. Cl.
CPC .............. G06F 30/00 (2020.01); A61F 11/06 (2013.01)

(58) Field of Classification Search
CPC .......... G06F 30/00; G06F 30/10; A61F 11/06; A61F 11/00; H04R 1/10; H04R 25/65;
(Continued)

(56) References Cited

U.S. PATENT DOCUMENTS 6,731,997 B2      5/2004  Hessel et al.
7,308,328 B2      12/2007  Fang et al.
(Continued)

FOREIGN PATENT DOCUMENTS

CN      106465025 A      2/2017
CN      106941652 A      7/2017
(Continued)

OTHER PUBLICATIONS

Response to Extended Search Report dated Nov. 7, 2023, from counterpart European Application No. 23170843.9 filed May 1, 2024, 14 pp.
(Continued)

*Primary Examiner* — Rasha S Al Aubaidi
(74) *Attorney, Agent, or Firm* — Shumaker & Sieffert, P.A.

(57)      ABSTRACT

A method comprises obtaining ear modeling data, wherein the ear modeling data includes a 3D model of an ear canal; applying a shell generation to generate a shell shape based on the ear modeling data, wherein the shell-generation model is a machine learning model and the shell shape is a 3D representation of a shell of an ear-wearable device; applying a set of one or more component-placement models to determine, based on the ear modeling data, a position and orientation of a component of the ear-wearable device, wherein the component-placement models are independent of the shell-generation model and each of the component-placement models is a separate machine learning model; and generating an ear-wearable device model based on the shell shape and the 3D arrangement of the components of the ear-wearable device.

16 Claims, 9 Drawing Sheets

(58) Field of Classification Search

CPC .......... H04R 25/00; H04R 5/02; G06T 19/00; G06T 7/73; G06N 20/00; G06K 9/62; G06V 10/764; B29C 67/00

See application file for complete search history.

(56) References Cited

U.S. PATENT DOCUMENTS

| | | | |
|---|---|---|---|
| 7,605,812 | B2 | 10/2009 | Mcbagonluri et al. |
| 7,801,708 | B2 | 9/2010 | Unal et al. |
| 7,961,981 | B2 | 6/2011 | Berg |
| 8,032,337 | B2 | 10/2011 | Deichmann et al. |
| 8,065,118 | B2 | 11/2011 | McBagonluri et al. |
| 8,069,022 | B2 | 11/2011 | Slabaugh et al. |
| 8,199,952 | B2 | 6/2012 | Boltyenkov et al. |
| 8,249,261 | B2 | 8/2012 | Kiepfer et al. |
| 9,433,373 | B2 | 9/2016 | Burns |
| 9,460,238 | B2 | 10/2016 | Hankey et al. |
| 10,032,463 | B1 | 7/2018 | Rastrow et al. |
| 10,158,954 | B1 | 12/2018 | Pirzanski |
| 10,284,975 | B2 | 5/2019 | Higgins et al. |
| 11,122,255 | B2 | 9/2021 | Fei et al. |
| 11,481,530 | B2 | 10/2022 | Zhang |
| 2002/0085728 | A1 | 7/2002 | Shennib et al. |
| 2003/0123685 | A1 | 7/2003 | Basseas |
| 2004/0107080 | A1 | 6/2004 | Deichmann et al. |
| 2007/0189564 | A1 | 8/2007 | Mcbagonluri et al. |
| 2008/0094392 | A1 | 4/2008 | McBagonluri et al. |
| 2008/0126062 | A1 | 5/2008 | Nikles et al. |
| 2009/0097682 | A1 | 4/2009 | Mcbagonluri et al. |
| 2009/0099677 | A1 | 4/2009 | McBagonluri et al. |
| 2015/0073262 | A1 | 3/2015 | Roth et al. |
| 2015/0271607 | A1 | 9/2015 | Sabin |
| 2020/0074662 | A1 | 3/2020 | Williams |
| 2020/0273248 | A1 | 8/2020 | Jorgensen et al. |
| 2020/0302099 | A1 | 9/2020 | Grenier et al. |
| 2021/0204076 | A1 | 7/2021 | Shonibare et al. |
| 2022/0414292 | A1 | 12/2022 | Zhang |

FOREIGN PATENT DOCUMENTS

| | | |
|---|---|---|
| CN | 108476352 A | 8/2018 |
| EP | 1345470 A2 | 9/2003 |
| EP | 1939776 A2 | 7/2008 |
| EP | 1368986 B1 | 12/2011 |
| EP | 2834750 B1 | 12/2017 |
| WO | 2002071794 A1 | 9/2002 |
| WO | 2006117408 A2 | 11/2006 |
| WO | 2020102722 A1 | 5/2020 |
| WO | 2020198023 A1 | 10/2020 |
| WO | 2021096873 A1 | 5/2021 |
| WO | 2021138603 A1 | 7/2021 |

OTHER PUBLICATIONS

Paulsen et al., "Statistical Shape Analysis of the Human Ear Canal with Application to In-the-Ear Hearing Aid Design", Technical University of Denmark, Nov. 1, 2004, 217 pp.

Paulsen et al., "Using a shape model in the design of hearing aids", Medical Imaging 2004: Image Processing, vol. 5370, May 12, 2004, pp. 1304-1311.

Sickel et al., "Toward Automation in Hearing Aid Design," Computer-Aided Design, vol. 43, Issue 12, Dec. 2011, 25 pp.

Slabaugh et al., "3-D Shape Modeling for Hearing aid Design", IEEE, vol. 25, No. 5, Sep. 2008, pp. 98-102.

Unal et al., "Customized Design of Hearing Aids Using Statistical Shape Learning", International Conference on Financial Cryptography and Data Security, Springer, Sep. 2008, pp. 518-526.

Unal et al., "Generating shapes by analogies: An application to hearing aid design", Computer-Aided Design, vol. 43, No. 1, Jan. 2011, 10 pp.

Extended Search Report from counterpart European Application No. 23170843.9 dated Sep. 20, 2023, 10 pp.

Communication pursuant to Article 94(3) EPC from counterpart European Application No. 23170843.9 dated Aug. 5, 2025, 7 pp.

Response to Communication pursuant to Article 94(3) EPC dated Aug. 5, 2025, from counterpart European Application No. 23170843.9 filed Jan. 27, 2026, 16 pp.

EAR-WEARABLE DEVICE MODELING

This application claims the benefit of U.S. Provisional Patent Application 63/363,870, filed Apr. 29, 2022, the entire content of which is incorporated by reference.

TECHNICAL FIELD

This disclosure relates to ear-wearable devices.

BACKGROUND

An ear-wearable device is a device designed to be worn on or in a user's ear. Example types of ear-wearable devices include hearing aids, earphones, earbuds, telephone earpieces, and other types of devices designed to be worn on or in a user's ear.

Some ear-wearable device manufacturers rely on highly skilled operators to design ear-wearable devices using three-dimensional modeling software. When an ear-wearable device is produced, these highly skilled operators and/or audiologists may make physical modifications to outer shells of the ear-wearable devices, for example, to ease user discomfort or otherwise shape the outer shells based on manufacturer or clinician needs. Manual modeling and shaping ear-wearable devices in this way is time consuming, expensive, and can lead to inconsistencies, e.g., due to variations in operator skill level and techniques.

SUMMARY

In general, this disclosure describes techniques for enabling a computing device to use machine-learning techniques to automatically generate, based on ear modeling data of an ear canal, an ear-wearable device model. As described herein, the computing system may apply a shell-generation model to generate a shell shape based on ear modeling data. The computing system may separately apply one or more component-placement models to determine a position and orientation of one or more components of the ear-wearable device. The shell-generation model and the component-placement models are machine learning models.

In one example, this disclosure describes a method comprising: obtaining, by a computing system comprising at least one processor implemented in circuitry, ear modeling data, wherein the car modeling data includes a 3D model of an car canal of a user; applying, by the computing system, a shell-generation model to generate a shell shape based on the car modeling data, wherein the shell-generation model is a machine learning (ML) model and the shell shape is a 3D representation of a shell of an car-wearable device to be worn in the car canal; applying, by the computing system, a set of one or more component-placement models to determine, based on the car modeling data, a position and orientation of a component of the car-wearable device, wherein the component-placement models are independent of the shell-generation model and each of the component-placement models is a separate machine learning model; and generating, by the computing system, based on the position and orientation of the component and the shell shape, an car-wearable device model that is specific to the user.

In another example, this disclosure describes a system comprising: one or more storage devices configured to store car modeling data, wherein the car modeling data includes a 3D model of an car canal of a user; one or more processors implemented in circuitry, the one or more processors configured to: apply a shell-generation model to generate a shell shape based on the car modeling data, wherein the shell-generation model is a machine learning (ML) model and the shell shape is a 3D representation of a shell of an car-wearable device to be worn in the car canal; apply a set of one or more component-placement models to determine, based on the car modeling data, a position and orientation of a component of the car-wearable device, wherein the component-placement models are independent of the shell-generation model and each of the component-placement models is a separate machine learning model; and generate, based on the position and orientation of the component and the shell shape, an car-wearable device model that is specific to the user.

In another example, this disclosure describes a non-transitory computer-readable storage medium having instructions stored thereon that, when executed, cause a computing system to: obtain car modeling data, wherein the car modeling data includes a 3D model of an car canal of a user; apply a shell-generation model to generate a shell shape based on the car modeling data, wherein the shell-generation model is a machine learning (ML) model and the shell shape is a 3D representation of a shell of an car-wearable device to be worn in the car canal; apply a set of one or more component-placement models to determine, based on the car modeling data, a position and orientation of a component of the car-wearable device, wherein the component-placement models are independent of the shell-generation model and each of the component-placement models is a separate machine learning model; and generate, based on the position and orientation of the component and the shell shape, an ear-wearable device model that is specific to the user.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
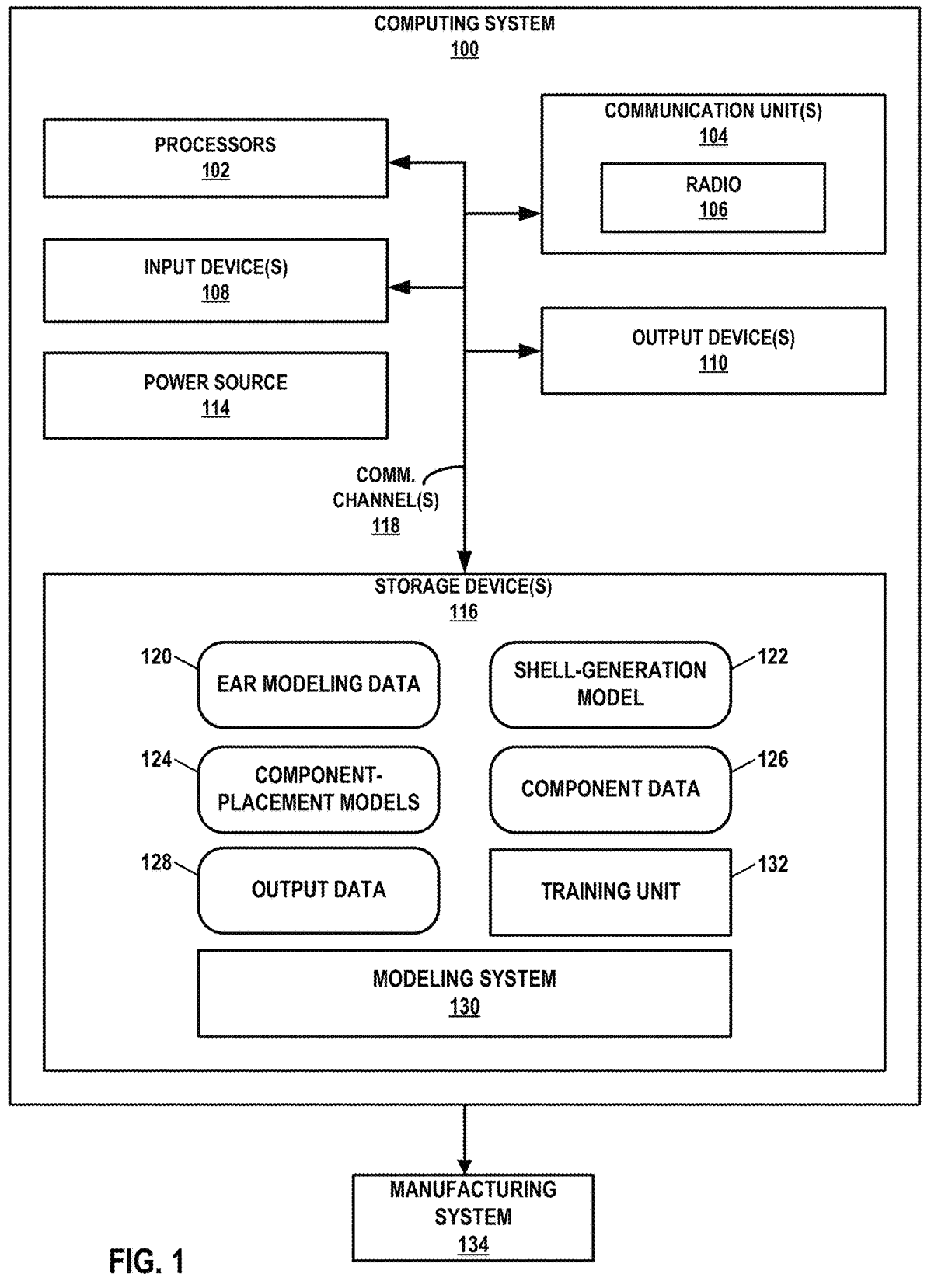
FIG. 1 is a conceptual diagram illustrating an example computing system, in accordance with one or more techniques of the present disclosure.

An ear-wearable device is a device designed to be worn on or in a user's ear. Example types of ear-wearable devices include hearing aids, earphones, earbuds, telephone ear-pieces, and other types of devices designed to be worn on or in a user's ear. As the term is used herein, an ear-wearable device, such as a hearing assistance device, a hearing device, and a hearing instrument, refers to any ear-wearable device that is used as a hearing aid, a personal sound amplification product (PSAP), a headphone set, a hearable, a wired or wireless earbud, or other hearing instrument that provides sound to a user for hearing.

Some ear-wearable device professionals take ear impressions of patients or end-users and send the raw impressions and/or scans of the raw impressions, along with other patient-specific requirements (e.g., style, features, etc.), to an ear-wearable device manufacturer facility. An operator (e.g., a production modeler, audiologist, etc.) at the manufacturing facility may scan the raw impressions or import the scanned impressions into three-dimensional modeling software.

Based on the patient-specific requirements and a set of empirical modelling guidelines known to the operator, the operator may manually design an ear-wearable device, for instance, by interacting with the modeling software to create a computer model of an outer shell that can contain all the internal components (e.g., microphones, receiver, circuits, vent, etc.) of the ear-wearable device and fit comfortably inside a particular user's ear. Even with the assistance of three-dimensional modeling software, a skilled operator may spend anywhere from five to fifteen minutes manually creating a model of an outer shell. Once the operator is satisfied with a shell design, an ear-wearable device is manufactured, based on the shell design. Afterwards, an operator at a manufacturing facility and/or an ear-wearable device professional at a clinic or retail location, may spend additional time further modifying the outer shell of the ear-wearable device (e.g., using hand tools) to minimize any actual, or foreseen, end-user discomfort.

Manual modeling and shaping ear-wearable devices in this way is time consuming, expensive, and can lead to inconsistencies, e.g., due to variations in operator skill level and operator techniques. If an end-user or professional would like to preview their custom, ear-wearable design before manufacturing, the clinic or retailer must have access to a dedicated modeler, expensive modeling software, and at least five to fifteen minutes of the modeler's time. Furthermore, for custom ear-wearable devices, such as over-the-counter hearing aids and such, costs and time associated with relying on human operators to manually create ear-wearable designs may not be feasible from a business standpoint and may inject delays in the procurement of ear-wearable devices, which may be unacceptable to a retailer, professional, or end-user.

In general, this disclosure describes techniques for enabling a computing device to use machine-learning techniques to automatically model ear-wearable devices. For example, some ear-wearable device manufacturers, and clinicians, have over time, accumulated hundreds of thousands if not millions of raw ear impressions and corresponding data associated with finished, ear-wearable device products.

The data may span a variety of ear-wearable device styles and other device and/or end-user characteristics. Rather than manually create car-wearable devices using operators and time-consuming modeling software, machine-learned models can be trained, using the accumulated ear impressions and corresponding data associated with finished ear-wearable devices, to output car-wearable device models that may mimic the finished, car-wearable devices created by skilled modelers and clinicians.

In accordance with one or more techniques of this disclosure, a computing system may obtain car modeling data. The car modeling data is a 3D model of an car canal of a user. The computing system may apply a shell-generation model to generate a shell shape based on the car modeling data. The shell-generation model is a machine learning (ML) model. The shell shape is a 3D representation of a shell of an ear-wearable device to be worn in the car canal of the user. The computing system may apply a set of one or more component-placement models to determine, based on the car modeling data, a position and orientation of a component of the car-wearable device. The component-placement models are independent of the shell-generation model and each of the component-placement models is a separate machine learning model. The computing system may generate an car-wearable device model based on the shell shape and the 3D arrangement of the components of the car-wearable device. Applying separate ML models for determining the shell shape and the arrangement of the components may improve stability of training processes of the ML models relative to a single ML model that generates the shell shape and the arrangement of the components. Moreover, applying separate ML models for determining the shell shape and the arrangement of the components may result in higher quality ear-wearable device models.

FIG. 1 is a conceptual diagram illustrating an example computing system 100, in accordance with one or more techniques of the present disclosure. Computing system 100 of FIG. 1 is configured to automatically model ear-wearable devices. Computing system 100 may include one or more computing devices. Example computing devices may include a computer workstation located at an ear-wearable device manufacturing facility. In some examples, computing system 100 may include one or more computing devices located at a clinic or other retail facility that fits and sells car-wearable devices to patients and other end users. In some cases, computing system 100 may include one or more computing devices in a cloud computing environment, and may be accessed remotely via a computing device located at a manufacturing facility, clinic, or other retail facility. In other examples, computing system 100 may include a mobile computing device associated with a patient or other end user. FIG. 1 illustrates only one particular example of components of computing system 100, and many other example configurations of computing device 100 may exist.

Computing system 100 is configured to generate a patient-specific model of an car-wearable device. The car-wearable device may comprise one of various types of devices that are configured to provide auditory stimuli to a user and that are designed for wear at, on, or near a patient. The car-wearable device may be worn, at least partially, in the car canal or concha. In any of the examples of this disclosure, each car-wearable device may comprise a hearing assistance device. Hearing assistance devices may include devices that help a user hear sounds in the user's environment. Example types of hearing assistance devices may include hearing aid devices, Personal Sound Amplification Products (PSAPs), and so on. In some examples, the car-wearable device is an over-the-counter device, a direct-to-consumer device, or a prescription device. Furthermore, in some examples, the ear-wearable device may provide auditory stimuli to a user that correspond to artificial sounds or sounds that are not naturally in the user's environment, such as recorded music, computer-generated sounds, sounds from a microphone remote from the user, or other types of sounds. For instance, the ear-wearable device may include a so-called "hearable," an earbud, or another type of device. Some types of hearing instruments provide auditory stimuli to the user corresponding to sounds from the user's environment and also artificial sounds. In some examples, the ear-wearable device uses a bone conduction pathway to provide auditory stimulation.

The ear-wearable device includes a shell that is designed to be worn in the ear and at least partially contains various components of the ear-wearable device, such as an electronics component, a receiver, a wax guard, and so on. Such hearing instruments may be referred to as in-the-ear (ITE), in-the-canal (ITC), completely-in-the-canal (CIC), or invisible-in-the-canal (IIC) devices. In some examples, the ear-wearable device may be a receiver-in-canal (RIC) hearing-assistance device, which include a housing worn behind the ear that contains electronic components and a housing worn in the ear canal that contains the receiver.

The ear-wearable device may implement a variety of features that may help the user hear better. For example, the ear-wearable device may amplify the intensity of incoming sound, amplify the intensity of incoming sound at certain frequencies, translate or compress frequencies of the incoming sound, and/or perform other functions to improve the hearing of the user. In some examples, the ear-wearable device may implement a directional processing mode in which the ear-wearable device selectively amplifies sound originating from a particular direction (e.g., to the front of the user) while potentially fully or partially canceling sound originating from other directions. In other words, a directional processing mode may selectively attenuate off-axis unwanted sounds. The directional processing mode may help users understand conversations occurring in crowds or other noisy environments. In some examples, the ear-wearable device may use beamforming or directional processing cues to implement or augment directional processing modes. In some examples, the ear-wearable device may reduce noise by canceling out or attenuating certain frequencies. Furthermore, in some examples, the ear-wearable device may help the user enjoy audio media, such as music or sound components of visual media, by outputting sound based on audio data wirelessly transmitted to ear-wearable device.

The ear-wearable device may include components that enable the ear-wearable device to communicate with other devices, such as another ear-wearable device, a smartphone, or another type of device. Example types of wireless communication technology include Near-Field Magnetic Induction (NFMI) technology, 900 MHZ technology, a BLUETOOTH™ technology, WI-FI™ technology, audible sound signals, ultrasonic communication technology, infrared communication technology, inductive communication technology, or another type of communication that does not rely on wires to transmit signals between devices. In some examples, the ear-wearable device uses a 2.4 GHz frequency band for wireless communication.

In the example of FIG. 1, computing system 100 includes one or more processors 102, one or more communication units 104, one or more input devices 108, one or more output devices 110, a power source 114, one or more storage devices 116, and one or more communication channels 118. Computing system 100 may include other components. For example, computing system 100 may include physical buttons, microphones, speakers, communication ports, and so on. Communication channel(s) 118 may interconnect each of processor(s) 102, communication unit(s) 104, input device(s) 108, output device(s) 110, and storage device(s) 116 for inter-component communications (physically, communicatively, and/or operatively). In some examples, communication channel(s) 118 may include a system bus, a network connection, an inter-process communication data structure, or any other method for communicating data. Power source 114 may provide electrical energy to components processor(s) 102, communication unit(s) 104, input device(s) 108, output device(s) 110, and storage device(s) 116.

Storage device(s) 116 may store information required for use during operation of computing system 100. In some examples, storage device(s) 116 have the primary purpose of being a short-term and not a long-term computer-readable storage medium. Storage device(s) 116 may be volatile memory and may therefore not retain stored contents if powered off. Storage device(s) 116 may be configured for long-term storage of information as non-volatile memory space and retain information after power on/off cycles. In some examples, processor(s) 102 on computing system 100 read and may execute instructions stored by storage device(s) 116.

Computing system 100 may include one or more input devices 108 that computing system 100 uses to receive user input. Examples of user input include tactile, audio, and video user input. Input device(s) 108 may include presence-sensitive screens, touch-sensitive screens, mice, keyboards, voice responsive systems, microphones or other types of devices for detecting input from a human or machine.

Figure 2:
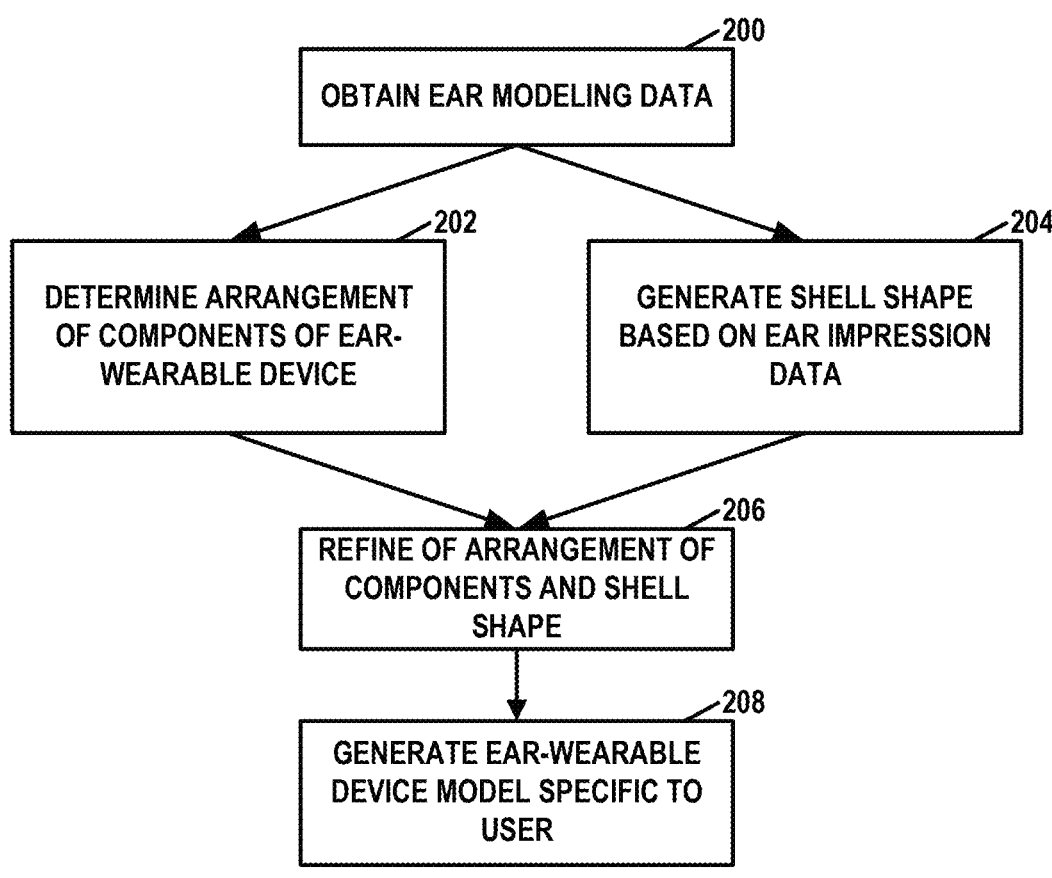
FIG. 2 is a flowchart illustrating an example process for generating a model of a patient-specific ear-wearable device, in accordance with one or more techniques of the present disclosure.

Communication unit(s) 104 may enable computing system 100 to send data to and receive data from one or more other computing devices (e.g., via a communications network, such as a local area network or the Internet). For instance, communication unit(s) 104 may be configured to receive data sent by hearing instrument(s) 102, receive data generated by a user of hearing instrument(s) 102, receive and send request data, receive and send messages, and so on. In some examples, communication unit(s) 104 may include wireless transmitters and receivers that enable computing system 100 to communicate wirelessly with the other computing devices. For instance, in the example of FIG. 1, communication unit(s) 104 include a radio 106 that enables computing system 100 to communicate wirelessly with other computing devices, such as ear-wearable device (FIG. 1). Examples of communication unit(s) 104 may include network interface cards, Ethernet cards, optical transceivers, radio frequency transceivers, or other types of devices that are able to send and receive information. Other examples of such communication units may include BLUETOOTH™, 3G, 4G, 5G, 6G, and WI-FI™ radios, Universal Serial Bus (USB) interfaces, etc. Computing system 100 may use communication unit(s) 104 to communicate with one or more hearing instruments (e.g., ear-wearable device (FIG. 1. FIG. 2)). Additionally, computing system 100 may use communication unit(s) 104 to communicate with one or more other remote devices.

Output device(s) 110 may generate output. Examples of output include tactile, audio, and video output. Output device(s) 110 may include presence-sensitive screens, sound cards, video graphics adapter cards, speakers, liquid crystal displays (LCD), or other types of devices for generating output. Output device(s) 110 may include a display screen.

Processor(s) 102 may read instructions from storage device(s) 116 and may execute instructions stored by storage device(s) 116. Execution of the instructions by processor(s) 102 may configure or cause computing system 100 to provide at least some of the functionality ascribed in this disclosure to computing system 100. As shown in the example of FIG. 1, storage device(s) 116 include ear modeling data 120, a shell-generation model 122, component-placement models 124, component data 126, and output data 128. Additionally, storage device(s) 116 may store computer-executable instructions associated with a modeling system 130 and a training unit 132. In other examples, storage device(s) 116 may store other types of data or types of computer-executable instructions. In some examples, such as examples where shell-generation model 122 and component-placement models 124 have already been trained, training unit 132 is not included in computing system 100.

Ear modeling data 120 includes a 3-dimensional (3D) model of an car of a patient. Although this disclosure refers to a patient, the techniques of this disclosure apply to car-wearable devices used for non-medical purposes. The 3D model of the car of the patient may represent an car canal of the patient. In some examples, the 3D model of the car of the patient may include other areas of the car of the patient, such as the concha, tragus, antitragus, incisura intertragica, antihelix, and so on.

Shell-generation model 122 includes a machine learning (ML) model that is trained to generate a 3D model of a shell of a patient-specific ear-wearable device (i.e., a shell shape). Component-placement models 124 may include ML models that are trained to predict positions and orientations of hardware components of the patient-specific car-wearable device. Example hardware components may include a receiver (i.e., a device for generating sound to be projected into the car canal of the patient), electronics components, a wax guard, and so on. Component data 126 may include data regarding sizes and types of components.

The electronics component may include processing circuitry, such as one or more microprocessors, digital signal processors, radios, charging circuitry, and so on. In some examples, the electronics component may also include a radio, data storage devices, and so on. The receiver may include one or more speakers configured to generate sound. The wax guard may include a screen and a screen support structure designed to prevent wax and other debris from entering the car-wearable device via a sound exit of the car-wearable device. The sound exit of the car-wearable device is a hole in the shell of the car-wearable device through which sound produced by the receiver passes on its way to the patient's ear drum.

Modeling system 130 is configured to generate output data 128. Output data 128 may include a model of an ear-wearable device based on ear modeling data 120. The car-wearable device may have a shell that is shaped specifically to fit an car canal of the patient. In accordance with one or more techniques of this disclosure, modeling system 130 may apply shell-generation model 122 to generate a shell shape for the car-wearable device based on car modeling data 120. In addition, modeling system 130 may apply component-placement models 124 to generate a 3D arrangement of the components of the car-wearable device. Modeling system 130 may refine the 3D arrangement of the components of the car-wearable device based on component data 126. Modeling system 130 may refine the shell shape based on the 3D arrangement of the components of the car-wearable device.

Thus, in accordance with one or more techniques of this disclosure, computing system 100 may obtain car modeling data 120. Ear modeling data 120 includes a 3D model of an ear canal of a user (e.g., a patient). Computing system 100 may apply a shell-generation model to generate a shell shape based on the ear modeling data. The shell-generation model is a ML model and the shell shape is a 3D representation of a shell of an ear-wearable device to be worn in the car canal. Computing system 100 may apply a set of one or more component-placement models to determine, based on the car modeling data, a position and orientation of a component of the ear-wearable device. The component-placement models are independent of the shell-generation model and each of the component-placement models is a separate machine learning model. The computing system may generate, based on the position and orientation of the component and the shell shape, an car-wearable device model that is specific to the user.

FIG. 2 is a flowchart illustrating an example process for generating a model of a patient-specific car-wearable device, in accordance with one or more techniques of the present disclosure. In the example of FIG. 2, computing system 100 may obtain car modeling data 120 (200). In some examples, computing system 100 obtains car modeling data 120 from a device that scans an ear of a patient. In some examples, computing system 100 obtain car modeling data 120 from a device that scans an car impression formed by inserting a moldable material into the car of the patient.

Modeling system 130 may change the format of car modeling data 120. For example, computing system 100 may obtain car modeling data 120 in a mesh format and modeling system 130 may change the format of car modeling data 120 to a 3D image format. In the 3D image format, car modeling data 120 includes a 3D array of voxels. Each voxel may indicate whether a corresponding location is open air or tissue of the patient. In some examples, modeling system 130 may define a bounding box that contains a portion of car modeling data 120 representing the patient's ear canal and excluding other, more lateral portions of the patient's ear, such as lateral portions of the patient's concha, the patient's tragus, antitragus, etc. Modeling system 130 may convert the mesh data within the bounding box into voxels. In some examples, car modeling data 120 is formatted as a point cloud. In some examples, modeling system 130 may use ear modeling data 120 in the mesh format as input to machine learning models that determine an arrangement of the components and generate a shell shape.

In some examples, modeling system 130 may change the orientation of ear modeling data 120. For instance, modeling system 130 may change the orientation of ear modeling data 120 so that the ear canal is oriented along the z-dimension. In some examples, modeling system 130 may scale, rotate, resample, or otherwise manipulate ear modeling data 120.

Modeling system 130 may apply a set of one or more component-placement models 124 to determine, based on ear modeling data 120, an arrangement of components of a patient-specific ear-wearable device (202). For instance, modeling system 130 may determine spatial position and orientations (i.e., arrangement) of each of a plurality of components of the patient-specific ear-wearable device. Such components may include an electronics unit, a receiver, a wax guard, sensor devices, microphones, and so on. As described in greater detail elsewhere in this disclosure, modeling system 130 may apply one or more ML models, including component-placement models 124, to generate the arrangement of the components of the patient-specific ear-wearable device.

Furthermore, in the example of FIG. 2, modeling system 130 may apply shell-generation model 122 to generate a shell shape of the patient-specific ear-wearable device based on ear modeling data 120 (204). The shell shape is a shape of a shell of the patient-specific ear-wearable device. The shell of the patient-specific ear-wearable device is an object that defines an enclosure to contain the components of the patient-specific ear-wearable device. The shell may have a shape configured to match the contours of an ear canal of the patient so that the patient-specific ear-wearable devices fits snugly within the ear canal of the patient. As described in greater detail elsewhere in this disclosure, modeling system 130 may apply one or more ML models, including shell-generation model 122, to generate the shell shape of the patient-specific ear-wearable device.

As shown in the example of FIG. 2, modeling system 130 may determine the arrangement of components of the patient-specific ear-wearable device and generate the shell shape of the patient-specific ear-wearable device independently. In some examples, modeling system 130 may determine the arrangement of components of the patient-specific ear-wearable device and generate the shell shape of the patient-specific car-wearable device in parallel.

In some examples, after determining the arrangement of the components and generating the shell shape, modeling system 130 may refine the arrangement of the components and the shell shape (206). For instance, as described in greater detail elsewhere in this disclosure, modeling system 130 may change the shell shape based on the arrangement of the components.

Additionally, modeling system 130 may output an ear-wearable device model that is specific to the patient (208). The ear-wearable device model may represent the arrangement of the components and the shell shape. In some examples, modeling system 130 may output the patient-specific ear-wearable device model for display to the patient and/or a clinician. For instance, the clinician may show the patient-specific ear-wearable device model to the patient during a consultation with the patient. In some examples, modeling system 130 may transfer the patient-specific ear-wearable device model to a coordinate space of ear modeling data 120. Thus, the patient-specific ear-wearable device model may be displayed along with car modeling data 120, e.g., to show the patient or clinician how the patient-specific ear-wearable device would fit into the patient's ear canal.

In some examples, modeling system 130 may output the model of the patient-specific ear-wearable device to a manufacturing system 134 (FIG. 1). Manufacturing system 134 may manufacture the shell of the car-wearable device and a component support structure configured to retain the component at the determined position and orientation. For instance, manufacturing system 134 may manufacture a component support structure that is configured to hold the components of the patient-specific ear-wearable device in the determined arrangement. Additionally, in some such examples, the components may be attached to the component support structure and immersed in a polymeric bath. A 3D printing apparatus of manufacturing system 134 may use a volumetric 3D printing process, such as holographic lithography or axial lithography to form a shell having the determined shell shape around the components. Additional details of this example manufacturing process are described in Patent Cooperation Treaty (PCT) publication WO 2021/096873, published May 20, 2021. In other examples, manufacturing system 134 may form the shell (e.g., using an additive manufacturing process or reductive manufacturing process) and a technician may insert the components into the shell.

Figure 3:
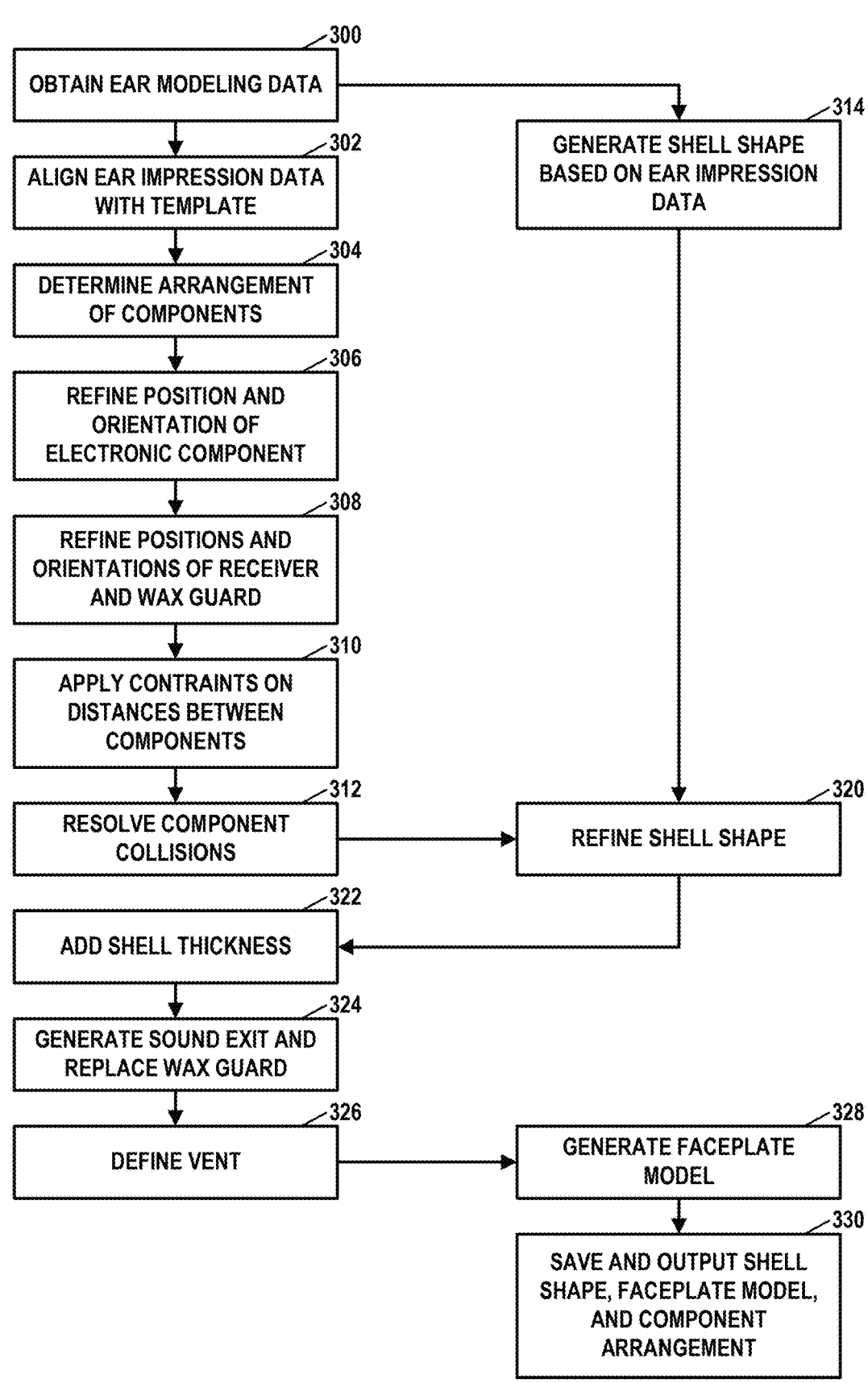
FIG. 3 is a flowchart illustrating an example process for generating a patient-specific hearing instrument model, in accordance with one or more techniques of the present disclosure.

FIG. 3 is a flowchart illustrating an example process for generating a patient-specific hearing instrument model, in accordance with one or more techniques of the present disclosure. The example of FIG. 3 shows additional example details of the process of FIG. 2. In the example of FIG. 3, modeling system 130 may obtain car modeling data 120 (300). Modeling system 130 may obtain and manipulate car modeling data 120 as described above with respect to FIG. 2.

In the example of FIG. 3, modeling system 130 may align car modeling data 120 with a template (302). A template may be 3D model of an ear canal. The template is not specific to the patient. For instance, modeling system 130 may perform a Nelder-Mead or Iterative Closest Point (ICP) method to determine a set of rotations that minimize differences in orientation and position between the car modeling data 120 and the template. Aligning car modeling data 120 with the template may help to reduce the influence of the orientation or position of car modeling data on an estimated arrangement of the components.

Furthermore, in the example of FIG. 3, modeling system 130 may apply one or more of component-placement models 124 to determine an arrangement of the components based on ear modeling data 120 (304). The components may include an electronics component, a receiver, and a wax guard. In some examples, such as the example of FIG. 4, described below, component-placement models 124 may include a positioning ML model and an orientation ML model for each of the electronics component, the receiver, and the wax guard. Thus, in this example, component-placement models 124 may include six ML models. Modeling system 130 may apply the positioning ML model for a component to determine a 3D position of the component based on ear modeling data 120. Modeling system 130 may apply the orientation ML model for a component to determine a 3D orientation of the component based on car modeling data 120 and the determined 3D position of the component. FIG. 5, which is described in greater detail elsewhere in this disclosure, illustrates an example structure of a component-placement model. In some examples, the same structure may be used for positioning ML models and orientation ML models. In other examples, different structures may be used for positioning ML models and orientation ML models. In examples where an ML model is a neural network model, modeling system 130 may apply the ML model by performing forward propagation of input data through the neural network model.

After estimating the arrangement of the components, modeling system 130 may refine the position and orientation of the electronics component (306). Additionally, modeling system 130 may refine the positions and orientations of the receiver and wax guard (308). In some examples, modeling system 130 refines the positions and orientations of the receiver and wax guard after refining the position and orientation of the electronics component because the electronics component may affect the external appearance of the patient-specific hearing instrument. As discussed in detail with respect to FIG. 4, modeling system 130 may apply refinement ML models to refine the orientations and positions of each of the components.

Furthermore, modeling system 130 may apply constraints on distances between the components (310). For example, modeling system 130 may check whether each of the components is at least a minimum distance another one of the components. In response to determining that the distance between two of the components is less than a minimum distance, modeling system 130 may incrementally increase the distance between the components while maintaining the orientations of the components until the distance between the components is greater than or equal to the minimum distance. In some examples, modeling system 130 may check whether a distance between two or more of the components exceeds a maximum distance. In response to determining that the distance between two of the components is greater than the maximum distance, modeling system 130 may incrementally decrease the distance between the components while maintaining the orientations of the components until the distance between the components is less than or equal to the maximum distance.

In some examples, as part of applying the constraints on the distances between the components, modeling system 130 may determine that there are collisions between two or more of the components or between any of the components and the skin of the car canal as represented in car modeling data 120. Accordingly, modeling system 130 may resolve the component collisions (312). For instance, in response to determining that there is a collision between two of the components, modeling system 130 may incrementally increase the distance between the components while maintaining the orientations of the components until the distance between the components is greater than or equal to a minimum distance. In response to determining that there is a collision between a component and the skin of the car canal, modeling system 130 may incrementally increase the distance between the component and the skin of the car canal until there is at least a minimum distance between the component and the skin of the car canal. Modeling system 130 may repeat the process of resolving collisions multiple times until there are no remaining collisions.

Figure 8:
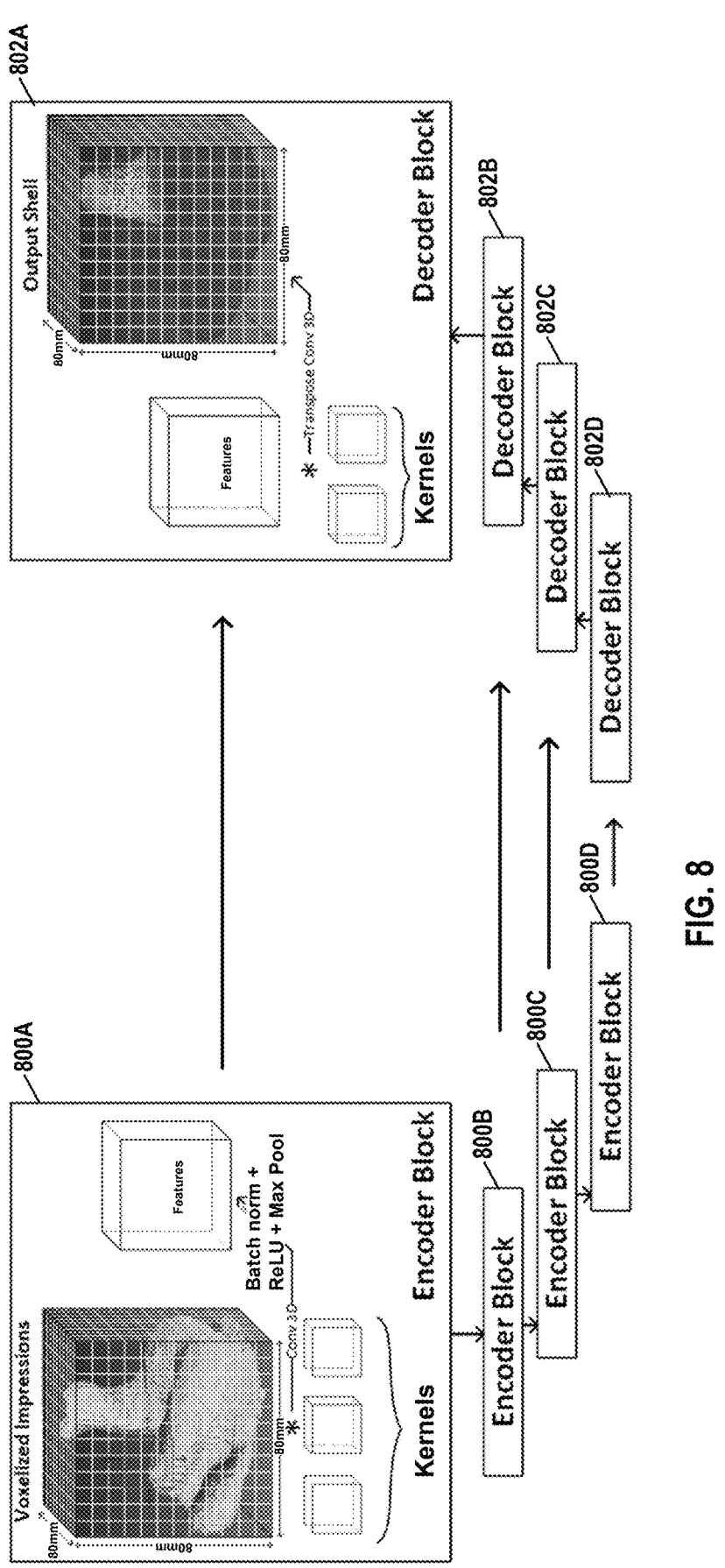
FIG. 8 is a conceptual diagram illustrating an example structure of a shell-generation model, in accordance with one or more techniques of the presenting disclosure.

Additionally, in the example of FIG. 3, modeling system 130 may generate a shell shape based on ear modeling data 120 (314). For example, modeling system 130 may apply shell-generation model 122 to generate the shell shape based on car modeling data 120. Shell-generation model 122 may generate a 3D image of the shell shape. In some examples, after generating the 3D image of the shell shape, modeling system 130 may convert the 3D image back into a mesh format. FIG. 8, which is described in greater detail elsewhere in this disclosure, illustrates an example structure of shell-generation model 122.

After generating the shell shape, modeling system 130 may refine the shell shape based on the arrangement of the components (320). For example, modeling system 130 may determine whether the arrangement of the components fits within the shell shape. In some instances, modeling system 130 may determine whether the arrangement of the components fits within the shell shape by determining whether there are any collisions between the shell shape and the arrangement of the components. If the arrangement of the components does not fit within the shell shape, modeling system 130 may increase a length of the shell shape into or out of the ear canal to accommodate the arrangement of components.

Additionally, modeling system 130 may add shell thickness to the shell shape (322). For instance, modeling system 130 may modify voxels of the 3D image of the shell thickness so that the 3D image of the shell represents the shell having a minimum thickness. In some examples, to modify the voxels, modeling system 130 may change a value of each respective voxel that is in a shell-wise interior direction from the existing shell shape and located within a given distance of a voxel in the existing shell shape to have a modified value indicating that the respective voxel is part of the shell shape.

Modeling system 130 may generate a sound exit and replace the wax guard (324). The wax guard may have a cylindrical shape. A medial rim of the wax guard (i.e., a rim of the wax guard that is oriented toward the medial plane of the patient) may be aligned with a medial surface of the shell shape. The medial surface of the shell shape may be a surface of the shell shape deepest in the patient's ear canal (e.g., a surface of the shell shape that is closest the medial plane of the patient). When generating the sound exit and replacing the wax guard, modeling system 130 may modify the shell shape so that the shell shape defines a cylindrical cavity configured to accommodate the wax guard. In other words, modeling system 130 may modify the shell shape to define a sound exit that accommodates the wax guard at the determined position and orientation of the wax guard. Sound generated by the receiver of the car-wearable device may exit the car-wearable device via a wax guard inserted into the cylindrical cavity. In other examples, the wax guard may have other shapes.

Additionally, modeling system 130 may modify the shell shape to define a vent (326). In other words, modeling system 130 automatically define a vent in the shell of the car-wearable device. The vent may allow sound generated within the patient's head to escape outward. Absence of a vent may result in excessive soundwaves reflecting from the car-wearable device toward the patient's eardrum. In some examples, to define the vent, modeling system 130 may identify locations on medial and lateral surfaces of the shell shape as openings of the vent. For instance, modeling system 130 may modeling system 130 may identify the superior-most locations on the medial and lateral surfaces as openings of the vent. Modeling system 130 may then determine a path (e.g., a shortest path) along an inner surface of the shell shape from the identified locations on the medial and lateral surfaces of the shell shape that does not intersect any of the components.

Modeling system 130 may generate a faceplate model for the car-wearable device (328). The faceplate model is a model of a faceplate shaped to cover a lateral opening of the shell surface. Modeling system 130 may generate the faceplate model based on the refined shell shape, as modified to include the vent. For instance, modeling system 130 may determine a shape of the lateral opening and generate a faceplate model to have an outline matching the shape of the lateral opening with a notch or hole for the lateral opening of the vent.

After generating the faceplate model, modeling system 130 may generate, based on positions and orientations of the components and the shell shape, an car-wearable device model that is specific to the patient (332). Modeling system 130 may generate the car-wearable device model as a combination of the shell shape, the faceplate model, and the positions and orientations of the components (i.e., the arrangement of the components). In some examples, the car-wearable device model may also include the faceplate model. Modeling system 130 may save the shell shape, the faceplate model, and the component arrangement as output data 128. In some examples, a display screen (e.g., one of output devices 110) displays the car-wearable device model.

Figure 4:
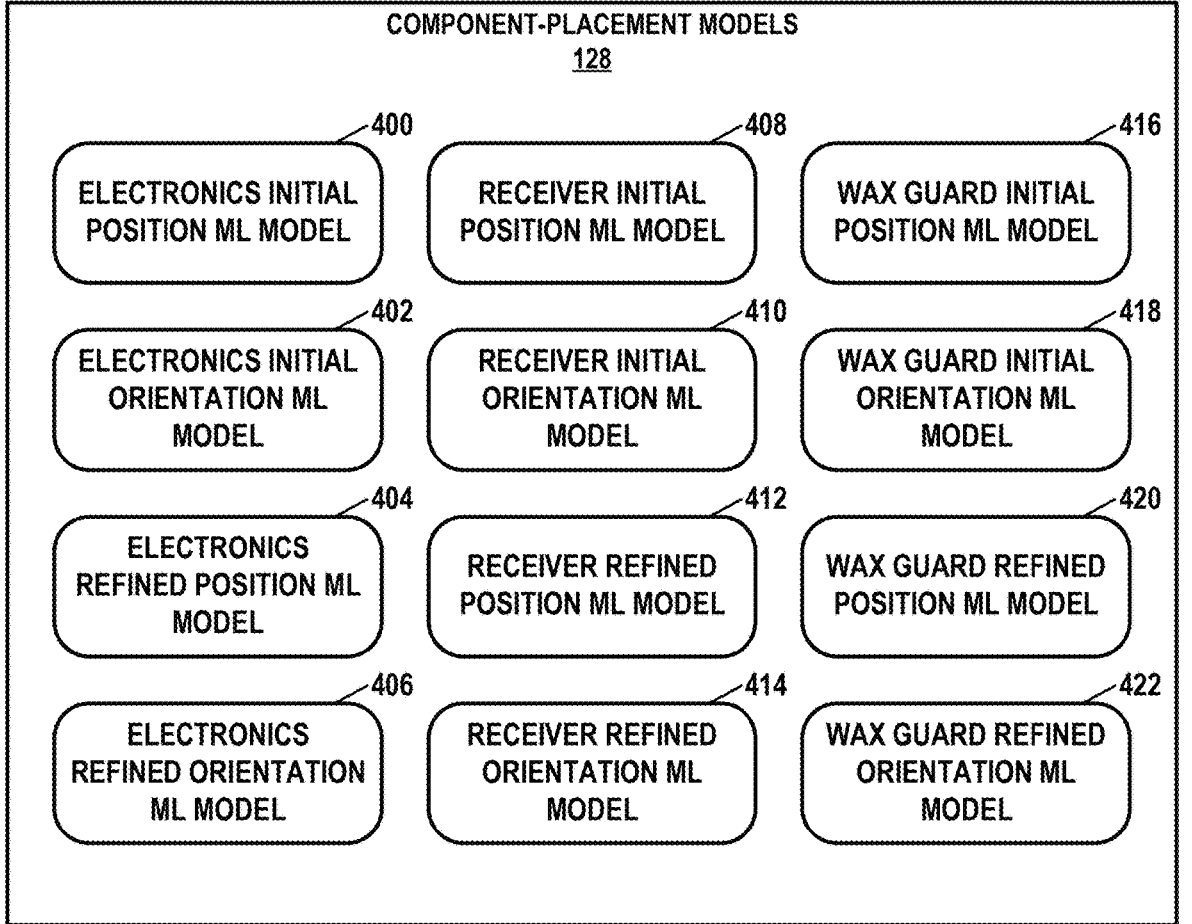
FIG. 4 is a block diagram illustrating example component-placement models, in accordance with one or more techniques of this disclosure.
Figure 5:
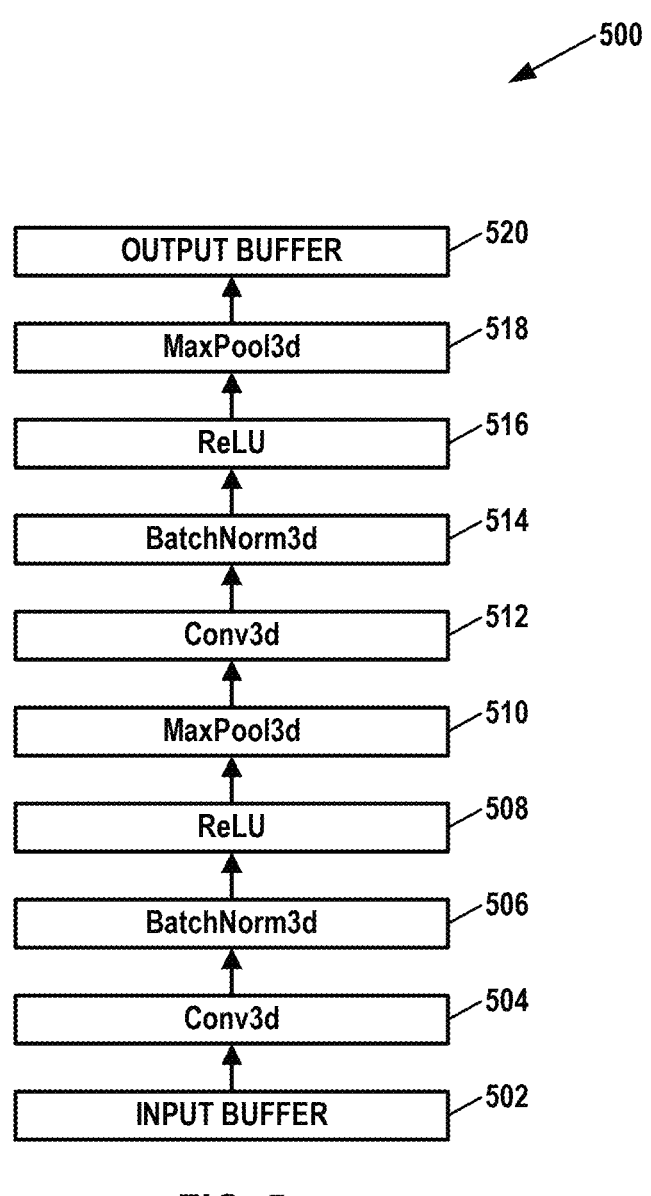
FIG. 5 is a conceptual diagram illustrating an example structure of a component-placement model, in accordance with one or more techniques of the present disclosure.

FIG. 4 is a block diagram illustrating example component-placement models 124, in accordance with one or more techniques of this disclosure. In the example of FIG. 4, component-placement models 124 may include an electronics initial position ML model 400, an electronics initial orientation ML model 402, an electronics refined position ML model 404, an electronics refined orientation ML model 406, a receiver initial position ML model 408, a receiver initial orientation ML model 410, a receiver refined position ML model 412, a receiver refined orientation ML model 414, a wax guard initial position ML model 416, a wax guard initial orientation ML model 418, a wax guard refined position ML model 420, and a wax guard refined orientation ML model 422.

Modeling system 130 may apply electronics initial position ML model 400 to determine an initial position of an electronics component based on car modeling data 120. Modeling system 130 may apply electronics initial orientation ML model 402 to determine an initial orientation of the electronics component based on car modeling data 120 and, in some examples, the initial position of the electronics component. Modeling system 130 may apply receiver initial position ML model 408 to determine an initial position of a receiver based on ear modeling data 120. Modeling system 130 may apply receiver initial orientation ML model 410 to determine an initial orientation of the receiver based on car modeling data 120 and, in some examples, the initial position of the receiver. Modeling system 130 may apply wax guard initial position ML model 416 to determine an initial position of a wax guard based on car modeling data 120. Modeling system 130 may apply wax guard initial orientation ML model 418 to determine an initial orientation of the wax guard based on car modeling data 120 and, in some examples, the initial position of the wax guard. Modeling system 130 may apply electronics initial position ML model 400, electronics initial orientation ML model 402, receiver initial position ML model 408, receiver initial orientation ML model 410, wax guard initial position ML model 416, and wax guard initial orientation ML model 418 as part of step 304 of FIG. 3 to estimate an arrangement of the components.

Furthermore, modeling system 130 may apply electronics refined position ML model 404 to determine a refined position of the electronics component based on car modeling data 120 and the initial position of the electronics component. Modeling system 130 may apply electronics refined orientation ML model 406 to determine a refined orientation of the electronics component based on car modeling data 120, the initial orientation of the electronics component, and component data 126 for the electronics component. Modeling system 130 may apply receiver refined position ML model 412 to determine a refined position of the receiver based on car modeling data 120, the initial position of the receiver, and component data 126 for the receiver. Modeling system 130 may apply receiver refined orientation ML model 414 to determine a refined orientation of the receiver based on car modeling data 120 and the initial orientation of the receiver. Modeling system 130 may apply wax guard refined position ML model 420 to determine a refined position of the wax guard based on car modeling data 120 and the initial position of the wax guard. Modeling system 130 may apply wax guard refined orientation ML model 406 to determine a refined orientation of the wax guard based on car modeling data 120, the initial orientation of the wax guard, and component data 126 for the wax guard. Modeling system 130 may apply electronics refined position ML model 404 and electronics refined orientation ML model 406 as part of step 306 of FIG. 3 to refine the position and orientation of the electronics component. Modeling system 130 may apply receiver refined position ML model 412, receiver refined orientation ML model 414, wax guard refined position ML model 420, and wax guard refined orientation ML model 422 as part of step 308 of FIG. 3 to refine the positions and orientations of the receiver and wax guard.

Determining the initial positions and orientations of the components using a first set of ML models followed by refining the positions and orientations of the components using a second set of ML models may improve the quality arrangement of the components.

Thus, in the example of FIG. 4, as part of applying one or more component-placement models to determine a position and orientation of a first component, modeling system 130 may apply a first component-placement model (e.g., electronics initial position ML model 400, receiver initial position ML model 408, or wax guard initial position ML model 416) to generate, based on the car modeling data, data indicating the position of the component. Modeling system 130 may apply a second component-placement model (e.g., electronics initial orientation ML model 402, receiver initial orientation ML model 410, or wax guard initial orientation ML model 418) to generate, based on the car modeling data and the data indicating the position of the component, data indicating the orientation of the component. Furthermore, in some examples, the data indicating positions of the components may be preliminary data and modeling system 130 may apply a component-placement model (e.g., electronics refined position ML model 404, receiver refined position ML model 412, or wax guard refined position ML model 420) to determine, based on the car modeling data and the preliminary data indicating the position of the component, refined data indicating the refined position of the component. Modeling system 130 may apply a component-placement model (e.g., electronics refined orientation ML model 406, receiver refined orientation ML model 414, or wax guard refined orientation ML model 422) to determine, based on the car modeling data and the preliminary data indicating the orientation of the component, refined data indicating the orientation of the component.

In some examples, the inputs to one or more of electronics refined position ML model 404, electronics refined orientation ML model 406, receiver refined position ML model 408, receiver refined orientation ML model 410, wax guard refined position ML model 420, and wax guard refined orientation ML model 422 may include component data 126. There may be several different available types of electronics components, receivers, and wax guards. The different types of these components may have somewhat different sizes and shapes. For example, if a patient has more profound hearing loss, a larger, more powerful receiver may be selected that is able to generate louder sounds. If the patient has less profound hearing loss, a smaller, less powerful receiver may be more appropriate. Similarly, electronics components with different capabilities may have somewhat different dimensions. Component data 126 may indicate which component types were selected for the patient. Component data 126 may indicate a selected component type in one or more ways. For instance, in some examples, component data 126 may include dimensional data of a selected component type. In some examples, component data 126 may include data indicating a model number of the selected component type. In some examples, instead of providing component data 126 as input to refinement ML models (e.g., electronics refined position ML model 404, electronics refined orientation ML model 406, receiver refined position ML model 408, receiver refined orientation ML model 410, wax guard refined position ML model 420, and wax guard refined orientation ML model 422), there may be different refinement ML models for each component type.

FIG. 5 is a conceptual diagram illustrating an example structure of a component-placement model 500, in accordance with one or more techniques of the present disclosure. Component-placement model 500 may be any of the component-placement models shown in the example of FIG. 4. In the example of FIG. 5, component-placement model 500 includes an input buffer 502 that contains input for component-placement model 500. For instance, input buffer 502 may include a 3D image of car modeling data 120. The 3D image of the car modeling data provided as input to electronics refined position ML model 404, electronics refined orientation ML model 406, receiver refined position ML model 412, receiver refined orientation ML model 414, wax guard refined position ML model 420, and wax guard refined orientation ML model 422 may represent the car canal of the patient and the corresponding component (e.g., electronics component, receiver, wax guard) at the initial positions and orientations determined by ML models 400, 402, 408, 410, 416, and 418. In some examples, input buffer 502 may include a 3D matrix of size 44×44×44 to store the 3D image of car modeling data 120. The 3D matrix of size 44×44×44 may represent a 22-millimeter (mm)×22 mm×22 mm bounding box. Data in input buffer 502 may be normalized to a 0 to 1 range.

A first convolutional layer 504 may apply a 3D convolution over data in input buffer 502. A first batch normalization layer 506 may apply batch normalization to the output of convolutional layer 504. A first Rectified Linear Unit (ReLU) layer 508 applies a ReLU activation function to output of batch normalization layer 506. A first max pooling layer 510 applies a 3D max pooling process to the output of ReLU layer 508. A second convolutional layer 512 applies a 3D convolution to the output of max pooling layer 510. A second batch normalization layer 514 may apply batch normalization to the output of second convolutional layer 512. A second ReLU layer 516 may apply the ReLU activation function to output of second batch normalization layer 514. A second max pooling layer 518 may apply the 3D max pooling process to the output of second ReLU layer 516. In other examples, activation functions other than the ReLU activation function may be used. Moreover, in some examples, different activation functions may be used in component-placement models for determining positions of components and in component-placement models for determining orientations of components. For instance, the ReLU activation function may be used in component-placement models for determining positions of components and a sigmoid activation function may be used in component-placement models for determining orientations of components.

An output buffer 520 may store the output of second max pooling layer 518. In instances where component-placement model 500 determines a position of a component, the output stored in output buffer 520 may include coordinate values indicating position in 3D space of the component. For instance, the output stored in output buffer 520 may include an x-coordinate, a y-coordinate, and a z-coordinate. In some examples, the coordinates correspond to a centroid of the component. In other examples, the coordinates may correspond to a landmark point on the component, such as a corner of the component. In instances where component-placement model 500 determines an orientation of a component, the output stored in output buffer 520 may include values that indicate an orientation of the component in the 3D space. For instance, the output stored in output buffer 520 may include angle values. In other instances, output stored in output buffer 520 may include a set of coordinates of a second point. A line from a point indicated by the coordinates determined for the position of the component and the second point corresponds to the orientation of the component.

Training unit 132 may train component-placement model 500. Training unit 132 may train component-placement model 500 based on training data. The training data may be based on records of arrangements of components in manually designed car-wearable devices. For example, the training data may include input-output pairs. The input of an input-output pair may include car modeling data 120. The input of an input-output may also include other information, such as a preliminary data indicating a position of a component, preliminary data indicating an orientation of a component, refined data indicating a position of a component, data indicating a component type, and so on. The output of an input-output pair may include data indicating a position or an orientation of a component. Training unit 132 may perform a forward propagation pass through component-placement model 500 using the input of an input-output pair. Training unit 132 may apply a loss function that generates a loss value based on the resulting output of component-placement model 500 and the output of the input-output pair. In some examples where component-placement model 500 determines a position of a component, the loss function calculates the loss value as a mean squared error of the differences between the position determined by component-placement model 500 and a position indicated by the output of the input-output pair. In some examples where component-placement model 500 determines an orientation of a component, the loss function calculates the loss value as a sum of differences between angles determined by component-placement model 500 and angles indicated by the output of the input-output pair.

Training unit 132 may use the loss value in a backpropagation process that may update weights and other parameters of component-placement model 500. During the backpropagation process, training unit 132 may use an Adam optimizer to perform stochastic gradient descent. Training unit 132 may use a learning rate of 0.001.

In some examples, training unit 132 may train component-placement model 500 using training data in which the input of the input-output pairs is based on car impressions formed by inserting a moldable material into cars of patients. Later training data may input-output pairs in which the input is based on optical scans of cars of patients. Rather than fully retrain component-placement model 500 using this later training data, training unit 132 may fix the weights of one or more layers of component-placement model 500 and only continue to modify weights of the last layer (e.g., layer 512) of component-placement model 500. This may be an example of transfer learning.

Figure 6:
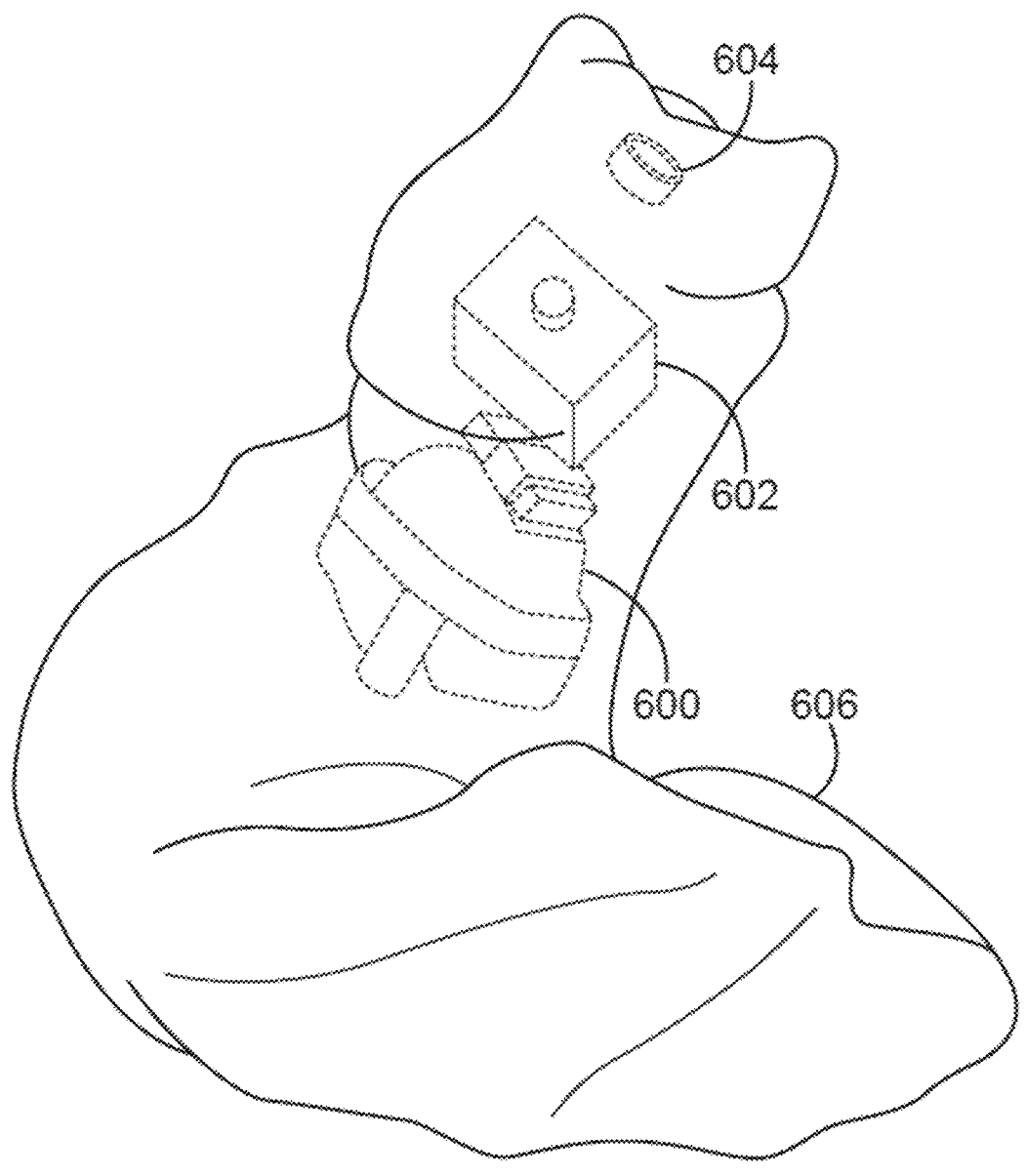
FIG. 6 is a conceptual diagram illustrating an example arrangement of components of an ear-wearable device, in accordance with one or more techniques of the present disclosure.

FIG. 6 is a conceptual diagram illustrating an example arrangement of components of an car-wearable device, in accordance with one or more techniques of the present disclosure. In the example of FIG. 6, an electronics component 600, a receiver 602, and a wax guard 604 are arranged within a shell 606. The shape of shell 606 may be patient specific.

Figure 7A:
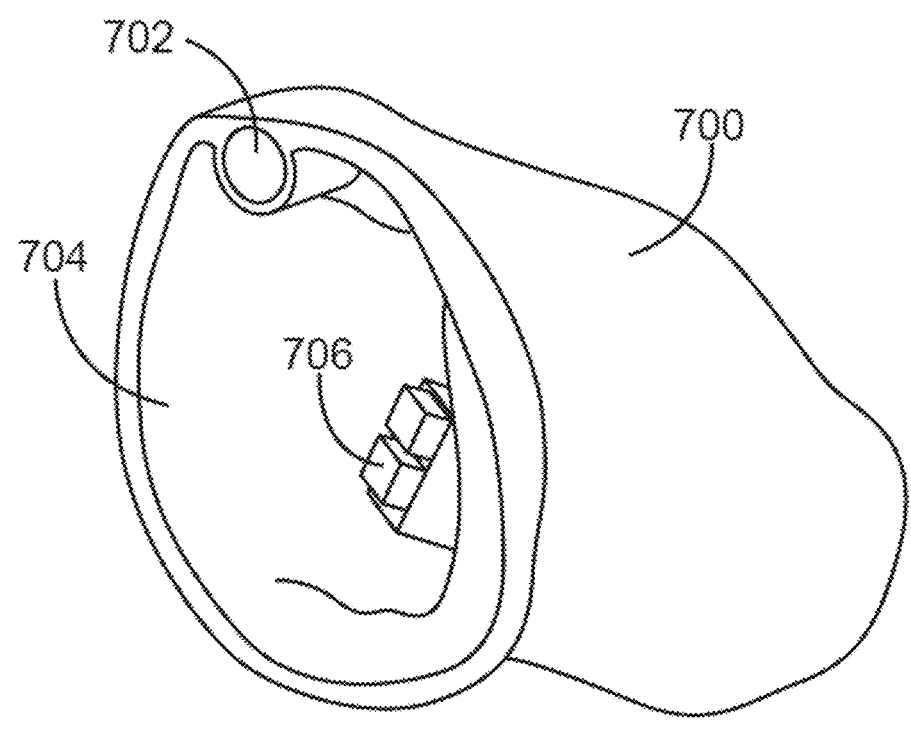
FIG. 7A and FIG. 7B are conceptual diagrams illustrating example vent placement, in accordance with one or more techniques of the present disclosure.
Figure 7B:
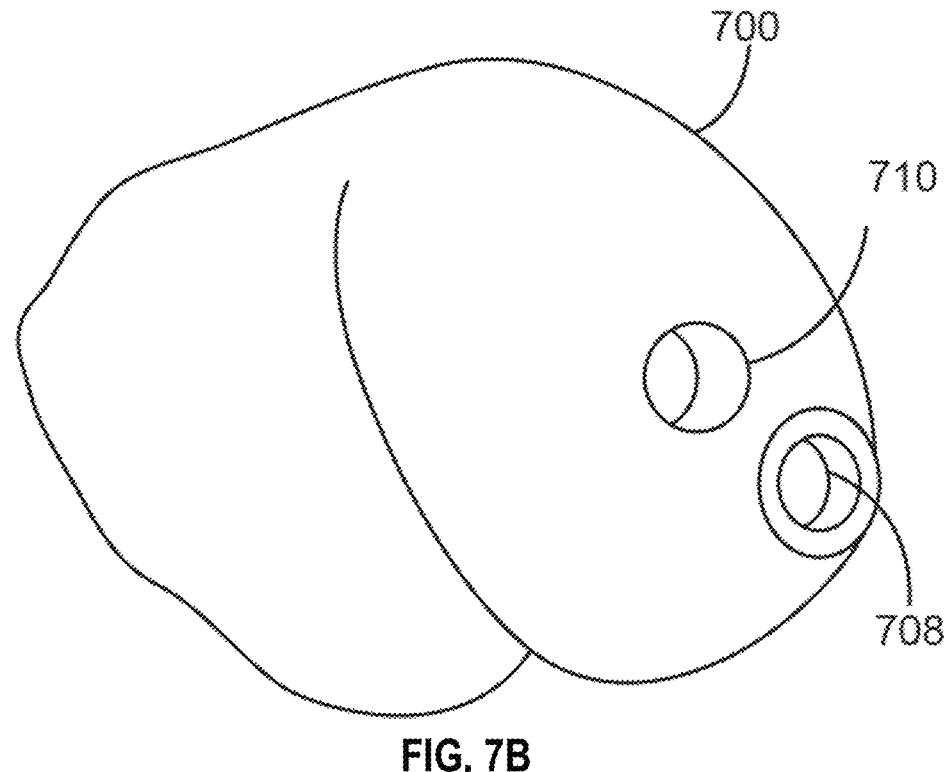

FIG. 7A and FIG. 7B are conceptual diagrams illustrating example vent placement, in accordance with one or more techniques of the present disclosure. FIG. 7A shows a shell 700 from a direction looking toward the medial plane of the patient. FIG. 7B shows shell 700 from a direction looking away from the medial plane of the patient. As shown in FIG. 7A, shell 700 defines a lateral vent opening 702. An interval cavity 704 defined by shell 700 includes components, such as an electronics component 706. As shown in FIG. 7B, shell 700 defines a sound exit 708 and a medial vent opening 710. A wax guard may be inserted into sound exit 708.

FIG. 8 is a conceptual diagram illustrating an example structure of shell-generation model 122, in accordance with one or more techniques of the presenting disclosure. In the example of FIG. 8, shell-generation model 122 has a U-net architecture. More specifically, shell-generation model 122 includes a set of encoder blocks 800A-800D (collectively, "encoder blocks 800") and a set of decoder blocks 802A-802E (collectively, "decoder blocks 802"). Encoder block 800A receives car modeling data 120 as a 3D image (i.e., a voxelized impression). In the example of FIG. 8, the 3D image represents a cube with 80 millimeters (mm) on each side. The output of encoder block 800A is a 3D feature array. Input to encoder block 800B may include the 3D feature array generated by encoder block 800A. Input to encoder block 800C may include a 3D feature array generated by encoder block 800B. Input to encoder block 800D may include a 3D feature array generated by encoder block 800C.

Encoder block 800A includes a set of one or more convolutional kernels. In the example of FIG. 8, encoder block 800A includes 3 convolutional kernels. In some examples, each of the convolutional kernels has a 1×1 convolution of stride length 2. Each of the convolutional kernels may be followed by a batch normalization (batch norm) layer, an activation layer (e.g., a ReLU activation layer), and a max pooling layer. Each of encoder blocks 800B, 800C, and 800D may have a similar structure of convolutional kernels and layers to encoder block 800A.

Input to decoder block 802D may be a 3D feature array generated by encoder block 800D. Input to decoder block 802C may include a 3D feature array generated by decoder block 802D concatenated with the 3D feature array generated by encoder block 800C. Input to decoder block 802B may include a 3D feature array generated by decoder block 802C concatenated with the 3D feature array generated by encoder block 800B. Input to decoder block 802A may include a 3D feature block generated by decoder block 802B concatenated with the 3D feature block generated by encoder block 800A. Decoder block 802A includes a set of transpose convolutional kernels. In the example of FIG. 8, decoder block 802A includes 2 transpose convolutional kernels. In some examples, each of the transpose convolutional kernels is a 1×1 up-convolution of stride length 2. Decoder block 802A may generate a 3D image of a shell shape (i.e., an output shell). Each of decoder blocks 802B, 802C, and 802D may have a similar structure to decoder block 802D with the exception that decoder blocks 802B, 802C, and 802D generate 3D feature arrays.

Training unit 132 may train shell-generation model 122. Training unit 132 may train component-placement models 124 separately from shell-generation model 122. As part of training shell-generation model 122, training unit 132 may obtain training data. The training data may include input-output pairs. For each of the input-output pairs, the input data may include a 3D image of an car canal. The output of an input-output pair may include a shell shape. The shell shape may be a 3D image of a shell. In some examples, training unit 132 obtains the training data from a database that contains patient records that include ear modeling data of the patients and shell shapes designed by human professionals.

Training unit 132 may perform forward propagation through shell-generation model 122 to generate a shell shape based on the car modeling data of an input of an input-output pair. Training unit 132 may then apply a loss function that generates a loss value based on the generated shell shape and the shell shape of the output of the input-output pair. Training unit 132 may use the loss value in a backpropagation process that updates weights within shell-generation model 122. In some examples, training unit 132 may determine the loss value used in the backpropagation process based on loss values generated by the loss function for multiple input-output pairs.

In some examples, the loss function may be intersection over union. In other words, training unit 132 may calculate a 3D area of the intersection between the generated shell shape and the shell shape of the output of the input-output pair. Additionally, training unit 132 may calculate a 3D area of the union of the generated shell shape and the shell shape of the output of the input-output pair. The union of these two shell shapes is the total area enclosed by the two shell shapes without double counting the intersection of the two shell shapes. Training unit 132 may calculate the loss value by dividing the intersection by the union. The loss value approaches 1 as generated shell shapes come to more closely match shell shapes in outputs of input-output pairs. The loss value approaches 0 for dissimilar shell shapes. During the backpropagation process, training unit 132 may perform gradient ascend to adjust the weights. In some examples, training unit 132 may use an Adam optimizer to adjust the weights during the backpropagation process. A learning rate of the Adam optimizer may be 0.001 or another value.

Figure 9:
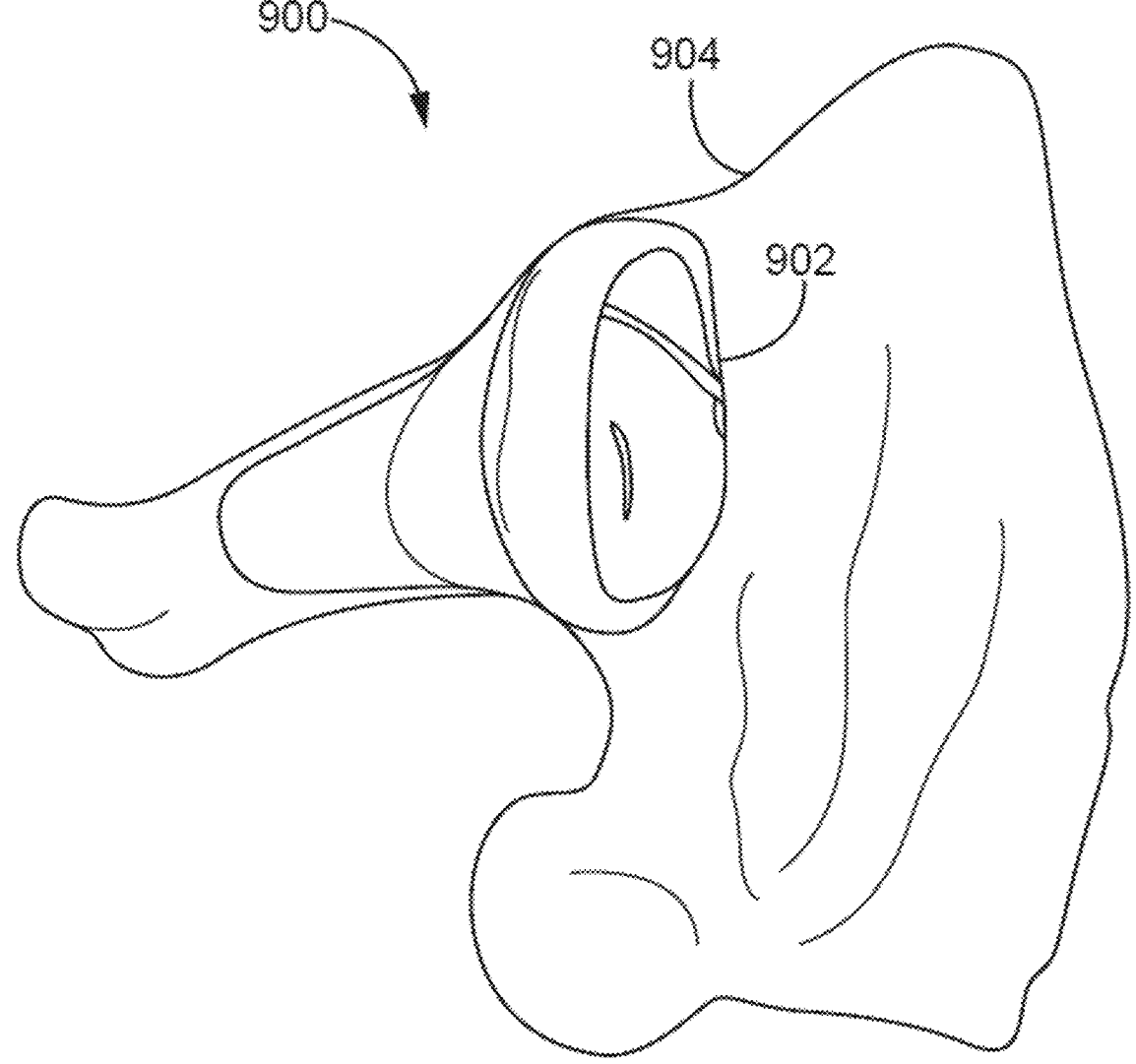
FIG. 9 is a conceptual diagram illustrating an example output of a modeling system showing a patient-specific ear-wearable device in a model of an ear of a patient, in accordance with one or more techniques of this disclosure.

FIG. 9 is a conceptual diagram illustrating an example output 900 of modeling system 130 showing a patient-specific car-wearable device 902 in a model 904 of an car of a patient, in accordance with one or more techniques of this disclosure. The patient or a clinician may review output 900 during a process of selecting or designing patient-specific car-wearable device 902.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection may be considered a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transitory, tangible storage media. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A method comprising:
obtaining, by a computing system comprising at least one processor implemented in circuitry, ear modeling data, wherein the ear modeling data includes a three-dimensional (3D) model of an ear canal of a user;
applying, by the computing system, a shell-generation model to generate a shell shape based on the ear modeling data, wherein the shell-generation model is a machine learning (ML) model and the shell shape is a 3D representation of a shell of an ear-wearable device to be worn in the ear canal;
applying, by the computing system, a first component-placement model to generate, based on the ear modeling data, data indicating a position of a component of the ear-wearable device, wherein the component is one of an electronics component, a receiver, or a wax guard;
applying, by the computing system, a second component-placement model to generate, based on the ear modeling data, data indicating an orientation of the component, wherein the first component-placement model and the second component-placement model are independent of the shell-generation model and each of the first component-placement model and the second component-placement model is a separate machine learning model; and
generating, by the computing system, based on the position of the component, the orientation of the component, and the shell shape, an ear-wearable device model that is specific to the user.

2. The method of claim 1, further comprising manufacturing the shell of the ear-wearable device and a component support structure configured to retain the component at the position and the orientation.

3. The method of claim 1, wherein the data indicating the position of the component is first preliminary data indicating the position of the component, the data indicating the orientation of the component is second preliminary data indicating the orientation of the component, and the method further comprises:
applying, by the computing system, a third component-placement model to determine, based on the ear modeling data and the first preliminary data indicating the position of the component, first refined data indicating a refined position of the component; and
applying, by the computing system, a fourth component-placement model to determine, based on the ear modeling data and the second preliminary data indicating the orientation of the component, second refined data indicating the orientation of the component.

4. The method of claim 1, further comprising:
training, by the computing system, the shell-generation model; and
training, by the computing system, the first component-placement model and the second component-placement model separately from the shell-generation model.

5. The method of claim 1, further comprising, after determining the position of the component and the orientation of the component, applying, by the computing system, constraints on distances between the component and one or more other components of the ear-wearable device.

6. The method of claim 1, wherein generating the ear-wearable device model comprises automatically defining, by the computing system, a vent in the shell of the ear-wearable device.

7. The method of claim 1, wherein the component is the wax guard and generating the ear-wearable device model comprises modifying, by the computing system, the shell shape to define a sound exit that accommodates the wax guard at the position and orientation of the wax guard.

8. The method of claim 1, wherein:
the component is a first component of a plurality of components of the ear-wearable device, and positions and orientations of the components are an arrangement of the components, and
the method further comprises:
applying, by the computing system, a second set of one or more component-placement models to determine, based on the ear modeling data, a position of a second component of the plurality of components and an orientation of the second component, wherein the second set of one or more component-placement models is independent of the first component-place-
ment model, the second component-placement
model, and the shell-generation model, and each of
the component-placement models in the second set
of one or more component-placement models is a
separate machine learning model; and
refining, by the computing system, the shell shape
based on the arrangement of the components.

9. A system comprising:
one or more storage devices configured to store ear
modeling data, wherein the ear modeling data includes
a three-dimensional (3D) model of an ear canal of a
user; and
one or more processors implemented in circuitry, the one
or more processors configured to:
apply a shell-generation model to generate a shell shape
based on the ear modeling data, wherein the shell-
generation model is a machine learning (ML) model
and the shell shape is a 3D representation of a shell
of an ear-wearable device to be worn in the ear canal;
apply a first component-placement model to generate,
based on the ear modeling data, data indicating a
position of a component of the ear-wearable device,
wherein the component is one or an electronics
component, a receiver, or a wax guard;
apply a second component-placement model to gener-
ate, based on the ear modeling data, data indicating
an orientation of the component, wherein the first
component-placement model and the second com-
ponent-placement model are independent of the
shell-generation model and each of the first compo-
nent-placement model and the second component-
placement model is a separate machine learning
model; and
generate, based on the position of the component, the
orientation of the component and the shell shape, an
ear-wearable device model that is specific to the user.
10. The system of claim 9, further comprising a manu-
facturing system configured to manufacture the shell of the
ear-wearable device and a component support structure
configured to retain the component at the position and the
orientation.
11. The system of claim 9, wherein the data indicating the
position of the component is first preliminary data indicating
the position of the component, the data indicating the
orientation of the component is second preliminary data
indicating the orientation of the component, and the one or
more processors are further configured to:
apply a third component-placement model to determine,
based on the ear modeling data and the first preliminary
data indicating the position of the component, first
refined data indicating a refined position of the com-
ponent; and
apply a fourth component-placement model to determine,
based on the ear modeling data and the second pre-
liminary data indicating the orientation of the compo-
nent, second refined data indicating the orientation of
the component.
12. The system of claim 9, wherein the one or more
processors are further configured to:
train the shell-generation model; and
train the first component-placement model and the second
component-placement model separately from the shell-
generation model.

13. The system of claim 9, wherein the one or more
processors are further configured to, after determining the
position of the component and the orientation of the com-
ponent, apply constraints on distances between the compo-
nent and one or more other components of the ear-wearable
device.
14. The system of claim 9, wherein the component is the
wax guard and the one or more processors are configured to,
as part of generating the ear-wearable device model, perform
at least one of:
automatically defining a vent in the shell of the ear-
wearable device, or
modifying the shell shape to define a sound exit that
accommodates the wax guard at the position and ori-
entation of the wax guard.
15. The system of claim 9, wherein:
the component is a first component of a plurality of
components of the ear-wearable device, and positions
and orientations of the components are an arrangement
of the components, and
the one or more processors are further configured to:
apply a second set of one or more component-place-
ment models to determine, based on the ear model-
ing data, a position of a second component of the
plurality of components and an orientation of the
second component, wherein the second set of one or
more component-placement models is independent
of the first component-placement model, the second
component-placement model, and the shell-genera-
tion model, and each of the component-placement
models in the second set of one or more component-
placement models is a separate machine learning
model; and
refine the shell shape based on the arrangement of the
components.
16. A non-transitory computer-readable storage medium
having instructions stored thereon that, when executed,
cause a computing system to:
obtain ear modeling data, wherein the ear modeling data
includes a 3D model of an ear canal of a user;
apply a shell-generation model to generate a shell shape
based on the ear modeling data, wherein the shell-
generation model is a machine learning (ML) model
and the shell shape is a 3D representation of a shell of
an ear-wearable device to be worn in the ear canal;
apply a first component-placement model to generate,
based on the ear modeling data, data indicating a
position of a component of the ear-wearable device,
wherein the component is one of an electronics com-
ponent, a receiver, or a wax guard;
apply a second component-placement model to generate,
based on the ear modeling data, data indicating an
orientation of the component, wherein the first compo-
nent-placement model and the second component-
placement model are independent of the shell-genera-
tion model and each of the first component-placement
model and the second component-placement model is a
separate machine learning model; and
generate, based on the position of the component and the
orientation of the component, and the shell shape, an
ear-wearable device model that is specific to the user.

* * * * *